(12) United States Patent
Barre et al.

(10) Patent No.: US 11,865,199 B2
(45) Date of Patent: Jan. 9, 2024

(54) METHOD FOR PROVIDING CONSUMER CHOICE AND EQUALIZING PHARMACY PROVIDER AVAILABILITY IN PRESCRIPTION MEDICATION DISPENSING PLANS

(75) Inventors: William J. Barre, Escondido, CA (US); Dale R. Brown, Poway, CA (US); Frederick Howe, Rancho Sante Fe, CA (US)

(73) Assignee: MEDIMPACT HEALTHCARE SYSTEMS, INC., San Diego, CA (US)

( * ) Notice: Subject to any disclaimer, the term of this patent is extended or adjusted under 35 U.S.C. 154(b) by 0 days.

(21) Appl. No.: 12/841,103

(22) Filed: Jul. 21, 2010

(65) Prior Publication Data
US 2010/0287002 A1  Nov. 11, 2010

Related U.S. Application Data

(62) Division of application No. 11/266,885, filed on Nov. 4, 2005, now abandoned.

(51) Int. Cl.
*A61K 8/66* (2006.01)
*A61Q 19/08* (2006.01)
(Continued)

(52) U.S. Cl.
CPC ............ *A61K 8/66* (2013.01); *A61K 8/732* (2013.01); *A61Q 19/08* (2013.01); *G06Q 30/06* (2013.01); *G06Q 40/08* (2013.01); *G16H 20/10* (2018.01)

(58) Field of Classification Search
CPC .......... A61K 8/66; A61K 8/732; A61Q 19/08; G06Q 30/06; G06Q 50/22
See application file for complete search history.

(56) References Cited

U.S. PATENT DOCUMENTS 5,301,105 A    4/1994   Cummings, Jr.
5,704,044 A   12/1997   Tarter et al.
(Continued)

FOREIGN PATENT DOCUMENTS

JP      2003-263499     9/2003
KR   10-2001-0075839    8/2001
(Continued)

OTHER PUBLICATIONS

PCT/US 06/42976, Jul. 8, 2007, PCT International Search Report.
(Continued)

*Primary Examiner* — Eliza A Lam
(74) *Attorney, Agent, or Firm* — Mintz, Levin, Cohn, Ferris, Glovsky and Popeo, P.C.

(57) ABSTRACT

A method is disclosed whereby consumers enrolled in a prescription benefit plan can obtain prescription medication fulfillment at any participating pharmacy of their choice, regardless of whether the fulfillment is by a retail pharmacy or a mail order pharmacy, and whether the quantity of medication prescribed is for administration over a short period (acute care) or a prolonged period (maintenance). The plan of this invention operates by having the plan manager substantially equalize the financial effects of the discounts and services fees allowed to participating pharmacies such that both retail and mail order pharmacies are compensated in a manner which encourages them to accept all consumers and fill all prescriptions. Compensation is preferably adjusted periodically by the manager to retain pharmacy incentives. Consumers obtain choice of pharmacies, plan payers have pleased employees and members and pharmacies obtain income from the entire spectrum of consumers.

3 Claims, 2 Drawing Sheets

(51) Int. Cl.
| | |
|---|---|
| G06Q 30/06 | (2023.01) |
| A61K 8/73 | (2006.01) |
| G16H 20/10 | (2018.01) |
| G06Q 40/08 | (2012.01) |

(56) References Cited

U.S. PATENT DOCUMENTS

| | | | |
|---|---|---|---|
| 5,737,539 A | 4/1998 | Edelson et al. | |
| 5,845,255 A | 12/1998 | Mayaud | |
| 6,108,635 A | 8/2000 | Herren et al. | |
| 6,195,612 B1 | 2/2001 | Pack-Harris | |
| 6,283,761 B1 | 9/2001 | Joao | |
| 6,341,265 B1 | 1/2002 | Provost et al. | |
| 7,165,077 B2 | 1/2007 | Kalies | |
| 7,412,396 B1 | 8/2008 | Haq | |
| 7,490,047 B2 | 2/2009 | Brown et al. | |
| 7,505,917 B2 | 3/2009 | Howe et al. | |
| 7,685,026 B1 | 3/2010 | McGrady et al. | |
| 7,769,601 B1 | 8/2010 | Bleser et al. | |
| 7,840,424 B2 | 11/2010 | Wiley et al. | |
| 7,949,580 B1 | 5/2011 | Boyer et al. | |
| 8,060,379 B1 | 11/2011 | Pinsonneault et al. | |
| 8,069,059 B2 | 11/2011 | Howe et al. | |
| 8,099,295 B2* | 1/2012 | Virdee et al. | 705/2 |
| 8,265,950 B2 | 9/2012 | Howe et al. | |
| 8,346,571 B2 | 1/2013 | Kalies, Jr. | |
| 8,447,628 B2 | 5/2013 | Kalies, Jr. | |
| 8,788,282 B2 | 7/2014 | Watanabe | |
| 2001/0037216 A1 | 11/2001 | Oscar et al. | |
| 2002/0002495 A1 | 1/2002 | Ullman | |
| 2002/0049617 A1 | 4/2002 | Lencki et al. | |
| 2002/0082863 A1 | 6/2002 | Kleinke | |
| 2002/0095316 A1 | 7/2002 | Toan et al. | |
| 2002/0111832 A1 | 8/2002 | Judge | |
| 2002/0120473 A1 | 8/2002 | Wiggins | |
| 2002/0147617 A1 | 10/2002 | Schoenbaum et al. | |
| 2002/0169727 A1 | 11/2002 | Melnick et al. | |
| 2002/0183965 A1 | 12/2002 | Gogolak | |
| 2003/0154106 A1 | 8/2003 | Marks | |
| 2003/0195771 A1 | 10/2003 | Fitzgerald et al. | |
| 2004/0039604 A1 | 2/2004 | Tallal, Jr. | |
| 2004/0054685 A1 | 3/2004 | Rahn et al. | |
| 2004/0073457 A1 | 4/2004 | Kalies | |
| 2004/0122713 A1 | 6/2004 | Hill et al. | |
| 2004/0133452 A1 | 7/2004 | Denny et al. | |
| 2004/0143171 A1 | 7/2004 | Kalies | |
| 2004/0143594 A1 | 7/2004 | Kalies | |
| 2004/0148194 A1 | 7/2004 | Wellons et al. | |
| 2004/0148195 A1 | 7/2004 | Kalies | |
| 2004/0148196 A1 | 7/2004 | Kalies | |
| 2004/0148198 A1 | 7/2004 | Kalies | |
| 2004/0148498 A1 | 7/2004 | Circenis et al. | |
| 2004/0230502 A1 | 11/2004 | Fiacco et al. | |
| 2005/0060188 A1* | 3/2005 | Valley | 705/2 |
| 2005/0065821 A1 | 3/2005 | Kalies, Jr. | |
| 2005/0071193 A1 | 3/2005 | Kalies | |
| 2005/0071200 A1* | 3/2005 | Franklin et al. | 705/3 |
| 2005/0240442 A1* | 10/2005 | Lapsker | 705/2 |
| 2005/0251429 A1 | 11/2005 | Ammer et al. | |
| 2005/0261939 A1 | 11/2005 | Augspurger et al. | |
| 2005/0283259 A1 | 12/2005 | Wolpow | |
| 2006/0020514 A1* | 1/2006 | Yered | 705/14 |
| 2006/0116905 A1* | 6/2006 | Yered | 705/2 |
| 2006/0129357 A1 | 6/2006 | Francis et al. | |
| 2006/0178915 A1 | 8/2006 | Chao | |
| 2006/0182705 A1 | 8/2006 | Cruse | |
| 2006/0184391 A1 | 8/2006 | Barre et al. | |
| 2006/0271402 A1 | 11/2006 | Rowe et al. | |
| 2007/0011025 A1 | 1/2007 | Cracchiolo et al. | |
| 2007/0025031 A1 | 2/2007 | Kwon | |
| 2007/0050210 A1 | 3/2007 | Wiley, II | |
| 2007/0106623 A1 | 5/2007 | Melnick et al. | |
| 2007/0233516 A1 | 10/2007 | Howe et al. | |
| 2007/0233526 A1 | 10/2007 | Hoffman et al. | |
| 2007/0250341 A1 | 10/2007 | Howe et al. | |
| 2008/0183492 A1 | 7/2008 | Warren et al. | |
| 2008/0228519 A1 | 9/2008 | Leon | |
| 2008/0312956 A1 | 12/2008 | Momita et al. | |
| 2009/0076868 A1 | 3/2009 | Malone et al. | |
| 2009/0144082 A1 | 6/2009 | Selbst et al. | |
| 2009/0177488 A1 | 7/2009 | Unland et al. | |
| 2009/0177490 A1 | 7/2009 | Howe et al. | |
| 2009/0281823 A1 | 11/2009 | Hardaway | |
| 2009/0281824 A1 | 11/2009 | Hardaway | |
| 2009/0319311 A1 | 12/2009 | Mi et al. | |
| 2009/0326975 A1 | 12/2009 | Hardaway et al. | |
| 2010/0057489 A1 | 3/2010 | Howe et al. | |
| 2010/0161351 A1 | 6/2010 | Howe et al. | |
| 2010/0217622 A1 | 8/2010 | Brown et al. | |
| 2010/0312578 A1 | 12/2010 | Hardaway | |
| 2011/0029321 A1 | 2/2011 | Rourke et al. | |
| 2011/0054935 A1 | 3/2011 | Hardaway | |
| 2012/0253829 A1 | 10/2012 | John et al. | |
| 2014/0278495 A1 | 9/2014 | Rourke et al. | |
| 2016/0034668 A1 | 2/2016 | Rourke et al. | |
| 2017/0161458 A1 | 6/2017 | Rourke et al. | |

FOREIGN PATENT DOCUMENTS

| | | |
|---|---|---|
| WO | WO 95/24010 | 9/1995 |
| WO | WO 97/44752 | 11/1997 |
| WO | WO-2014/151911 | 9/2014 |

OTHER PUBLICATIONS

Laing, R. O., et al., "Tuberculosis Drug Issues: Prices, Fixed Dose Combination Products and Second Line Drugs", *Journal Tuberculosis Disease*, 4(12) S194-S207 (Feb. 2000).

Huskamp, H.A., et al., "The Medicare Prescription Drug Benefit: How Will the Game be Played?" *Health Affairs*, 19(2) 8-23 (Mar./Apr. 2000).

Lipton, H.L., et al., "Managing the Pharmacy Benefit in Medicare HMOs: What Do We Really Know?" Health Affairs, 19(2) 42-58 (Mar./Apr. 2000).

"Cost Sharing Strategies for OHP Medical Services." pp. 1-5. Revised Jul. 5, 2001.

MedImpact Medicare Part D 2009 Pre-Processing Drug List (PPDL) White Paper, Updated Mar. 25, 2008. pp. 1-5.

MedImpact Medicare Part D 2008 Pre-Processing Drug List (PPDL) White Paper, Updated Mar. 25, 2008. pp. 1-5.

MedImpact Medicare Part D Pre-Processing Drug List (PPDL) White Paper, Updated Jul. 20, 2006. pp. 1-5.

MedImpact Medicare Part D Drug List White Paper, Oct. 13, 2005. pp. 1-4.

AMCP Guide to Pharmaceutical Payment Methods; Comperhensive Edition; AMCP Task Force on Drug Payment Methodologies; Oct. 2007 (65 pages).

"CVS to Buy MinuteClinic Walk-In Medical Service", Los Angeles Times, Jul. 14, 2006 (1 page).

Bank of America and Caremark introduce pharma rewards credit card, Oct. 27, 2006 http://www.banking-business-review.com/news/bank_of_america_and_caremark_introduce_pharma_r (1 page).

Centers for Medicare & Medicaid Services (CMS), 2006 Prescription Drug Event Data Training Participant Guide, Jul. 2006, pp. 1-222.

CitiBusiness Credit Cards Free Prescription Discount Program, May 11, 2006 07:14 AM Pacific http://www. payments news.com/2006/05/citibusiness_cr.html (3 pages).

CitiBusiness(R) Credit Cards Announces New Cardmember Benefit Free Prescription Discount Program, May 11, 2006, http:/Mw-N.prnewswire.com/cgi-bin/stories.pl?ACCT=104&STORY=/ww (2 pages).

Credit Cards Offer Discounts on Prescription Drugs, Mar. 26, 2008, http://wbztv.com/consumer/credit.Card.Discounts.2.682345.html (2 pages).

Florida House of Representatives, Enrolled CS/HB 535, 2008 Legislature (5 pages).

PCT International Preliminary Report on Patentability for Application No. PCT/US2014/026660 dated Sep. 24, 2015 (7 pages).

(56) References Cited

OTHER PUBLICATIONS

PCT International Search Report and Written Opinion for Application No. PCT/US2014/026660 dated Aug. 4, 2014 (9 pages).
PCT International Search Report and Written Opinion for Application No. PCT/US06/42976 dated Jul. 8, 2007. (17 pages).
Prescription Card, Jun. 6, 2009 (print date) http://www.unionplus.org/health/health-savings/prescription-card (2 pages).
Systems Xcellence Announces Three-Year $4.0 Million Software License, Support and Operations Contract, Nov. 9, 2005 http://www.eprescribingnews.com/archives/2005/11/reta (2 pages).
Walgreens Store Green Dot Prepaid MasterCard and Visa cards, Jun. 10, 2009 http://www.walgreens.com/store/promotion/greendot/default.jsp (2 pages).
Infocrossing Healthcare Services, Inc., Prescription Drug Event (PDE) Submission Process Summary, 2007, Infocrossing, pp. 1-2.
Comments of Generic Pharmaceutical Association for the Public Meeting on Proposed Changes to the National Drug Code System; RIN 0910-AA49; Nov. 24, 2006; 7 pages.
Department of Health and Human Services, Requirements for Submitting Prescription Drug Event Data, Apr. 27, 2006, Centers for Medicare and Medicaid Services, pp. 1-92.
Medicare Program: Revisions to the Medicare Advantage and Prescription Drug Benefit Programs; The Federal Register (FIND73.096); May 16, 2008; Source: Dept. of Health and Human Services.

\* cited by examiner

METHOD FOR PROVIDING CONSUMER CHOICE AND EQUALIZING PHARMACY PROVIDER AVAILABILITY IN PRESCRIPTION MEDICATION DISPENSING PLANS

RELATED APPLICATIONS

This application is a divisional of U.S. patent application Ser. No. 11/266,885, entitled METHOD FOR PROVIDING CONSUMER CHOICE AND EQUALIZING PHARMACY PROVIDER AVAILABILITY IN PRESCRIPTION MEDICATION DISPENSING PLANS, filed on Nov. 4, 2005, which is incorporated by reference, in its entirety.

FIELD OF THE INVENTION

The present invention relates generally to the field of filling prescriptions for consumers. More particularly it relates to prescription payment benefits made available by health plans, employer groups, governmental entities and other organizations to their employees and/or members.

BACKGROUND OF THE INVENTION

Many employees and members ("consumers") of health maintenance organizations, employer groups and government entities have their purchases of personal prescription medications subsidized by payments to pharmacies through prescription benefit plans ("plans") offered by those health maintenance organizations, employer groups and government entities. Under such plans, a consumer receives a prescription for a medication from his or her physician and submits it to a pharmacy to be filled. The pharmacy checks to see that the consumer is a member of a plan with which the pharmacy has a contract and that the medication and dosage prescribed are within the approved scope of the plan contract. Upon verification of these requirements, the pharmacy dispenses the medication to the consumer. The consumer pays the pharmacy a "copay" amount, less than the normal cost of the medication. The pharmacy receives the balance of the payment for the medication and its dispensing services from the prescription benefit plan, which is managed by a "prescription benefit manager" ("PBM") with whom the health maintenance organization, employer group or government entity ("payer") has contracted to manage the plan. The PBM invoices the payer (i.e., the PBM's customer) for the consumer's transaction, along with a charge for its contracted fee, and from the funds paid by the payer the PBM pays the pharmacy's balance due.

Medication usage is commonly differentiated between acute care usage, which is short term (30 days or less) administration to treat immediate illnesses or conditions, and maintenance usage, which is long term (more than 30 days) treatment of chronic illnesses or conditions such as hypertension, high cholesterol levels, arthritis, neurology conditions and the like. Maintenance medication dispensing and usage represents a major health care cost (on the order of 75% of prescription costs for many plans, especially due to the aging of the American population) and therefore control of maintenance prescription costs is a principal function of the prescription benefit plans. Dispensing pharmacies are normally of two types: retail pharmacies (which are local neighborhood businesses where the consumer appears in person, can meet with a pharmacist, orders his/her medication and can usually leaves a few minutes later with the dispensed medication in hand) and mail order pharmacies (which are large facilities, usually not open to individual consumer's personal visits, but from which a consumer's medication order received by mail or through the Internet is subsequently filled and dispensed to the consumer via mail or courier service). It is normally recognized by the industry that acute care prescriptions are dispensed primarily by retail pharmacies, since the consumer frequently needs the medication immediately and cannot accept the multi-day delay inherent in submitting and dispensing prescription medications from the mail order pharmacies.

On the other hand, PBMs and benefit consultants commonly strongly urge or even mandate that consumers in the plans that they administer obtain their maintenance medications from mail order pharmacies. It is a widely held belief that mail order pharmacies may have lower operating costs and may offer greater discounts available on medication coverage. To the extent that such is the case, use of mail order pharmacies may be a desirable cost control strategy if other contractual terms remain equalized. However, several factors can complicate the analysis of use of mail order pharmacies versus use of retail pharmacies especially for dispensing of maintenance medications. For instance, some PBMs own mail order pharmacies, and therefore it is to their financial benefit to steer the consumers in their plans to their captive pharmacies whether or not that is in the best interest of the consumers. Further, to the extent that business is diverted unreasonably from retail pharmacies to mail order pharmacies, the former are deprived of income. Since the retail pharmacies are commonly localized businesses (in contrast to mail order pharmacies), their ability to survive to provide the local retail service is impaired. This is true even when a local pharmacy is part of a larger chain pharmacy organization, since decline in income of a local site could lead the chain to close that local site, notwithstanding that other locations of the chain's pharmacies remain in business. Further, there are many variables in the pricing of medications and the costs involved in inventories, dispensing equipment, transportation of medications to the pharmacy and later to the consumer and staffing, that have been shown to affect whether mail order does or does not have a financial advantage over retail in the dispensing of medications. All that can be said is that, properly managed, both types can be financially and commercially viable.

Further, and very significantly, there is a question of availability of choice for the consumer, since in many cases a consumer would like to have the option of dealing either with his/her local pharmacy or a mail order pharmacy. Numerous studies have established that for many prescription consumers, direct contact with a pharmacist is very important. Professional pharmacists are held in very high regard by consumers and their advice is eagerly sought. Most consumers are not knowledgeable about medications and a prescribing physician's schedule may not provide sufficient time for a consumer to be able to get what he or she believes to be sufficient information from the prescribing physician about all aspects of concern about a prescribed medication. Consumers want to be able to speak directly to their pharmacists for more information about their medications and receive detailed answers to their questions and concerns, especially when a maintenance medication which will be taken by the consumer over a prolonged period is involved. It is well known that the prospects for a consumer's (patient's) successful implementation of a medication regimen are greatly enhanced when the consumer/patient understands and is comfortable with the medication prescribed. Such direct and personal contact with a pharmacist is frequently difficult for a consumer to obtain from a mail order pharmacy, and even when available will almost certainly not involve a pharmacist who is "local" to the consumer and his/her community.

Conventionally brand name prescriptions are priced by starting with a nationally published "average wholesale price" (AWP) and discounting this figure. A dispensing fee is then added to this number. A mail order or retail 90 day prescription is priced the same way with the exception that the mail order discounts are greater and there may or may not be a dispensing fee. On the other hand, in the prior art systems generic drug claims usually employ an additional variant for pricing. This is a concept known as "maximum allowable cost" (MAC) pricing. MAC is the concept of paying a set price for a product on a per unit basis. Since multiple manufacturers may produce the same generic drug and dosage, the MAC price is applied regardless of the manufacturer or that particular manufacturer's AWP. In the prior art plans, it is common that 30-day prescriptions are paid at the lower of a) AWP minus a discount plus a dispensing fee or b) MAC plus a dispensing fee, while 90-day prescriptions are paid solely at AWP minus a discount. In the common situation where mail order pharmacies do not fill 30-day prescriptions and many 90-day prescription consumers are routed by PBMs solely to mail order pharmacies, the system becomes biased, in that the consumer and payer may actually pay more for one 90-day prescription compared to the dispensing of three 30-day prescription for a particular medication dispensed. This leads to consumer and payer dissatisfaction. The payer has an expectation of budgeting for a set discount for 90 day prescriptions since is the traditional 90 day method for reimbursement. When a lower of MAC or AWP model is used a payer cannot guarantee an overall generic performance. The pharmacy has an expectation to be reimbursed a set amount for dispensing the 90 day prescription. When a lower of MAC or AWP model is used the pharmacy cannot be sure of its reimbursement.

Prescription care plans function by assigning a "processor control number" (PCN) to each consumer prescription claim. Since at present retail pharmacies typically dispense prescriptions in short-term (30-day or less) quantities and mail-order pharmacies dispense prescriptions in long-term (usually in either 60-day or 90-day) quantities, this means that a PBM is typically required to set up multiple PCNs for acute versus maintenance drug benefit designs, although each retail or mail order pharmacy is accustomed to identifying a single PCN to a consumer prescription claim for a specific payer's plan. As noted, consumers and payers want to be able to choose where they get prescriptions filled. However, when a pharmacy undertakes to dispense both short-term and long-term quantities, the pharmacist or pharmacy staff must now in effect choose between two PCNs for the same payer. Since the consumer only presents one identification card, this process can cause confusion at the pharmacy. This is counter productive to traditional workflow. It can cause confusion and delays at the point of sale transaction that impact both the consumer and the pharmacy. It may also reduce the number of 90-day supply prescriptions that are filled at the retail level which impacts the cost structure for the payer.

It is not the intention of the present invention to determine any conclusion as to the relative merits of mail order pharmacies versus retail pharmacies. Rather it is the intention of the present invention to meet the long-felt and widely expressed desire by consumers, payers and pharmacists to make both equally financially available under a prescription benefit plan such that consumers can have a legitimate choice as to where and how they obtain their prescription medications, the payers will have a legitimate choice about how their contract plans will be structured, and pharmacists in both types of pharmacies can practice their profession successfully.

SUMMARY OF THE INVENTION

For simplicity in the discussion below the invention will be described by division of prescription quantity fulfillments into two categories: a) "short term", "acute care" or "30-day" quantities, all of these terms being considered synonymous, and b) "long-term", "maintenance" or "90-day" quantities, all of these terms also being considered synonymous. Further, the terms "quantity", "quantity of dosage units" and "days supply" are also considered to be synonymous as applied to the number of medication pills, tablets, capsules, etc., or amount of medication liquid dispensed to the consumer upon fulfillment of the prescription request. It will be understood, however, that these terms are so used for brevity and convenience, and that regardless of the choice of terminology the method of the present invention is equally applicable to management of all prescription fulfillment and dispensing of medications in any dosages or quantities. Similarly, the particular total days supply of a dispensing prescription, whether the exemplary and commonly used 30- and 90-day quantities, or 14-, 60-, 100-day or any other quantities, is to be understood to be within the scope of the invention. Those skilled in the art will be readily able to calculate and apply the appropriate discount and other payments for any desired dispensed quantity or medication.

The present invention provides an innovative pharmacy-based program that allows employees/plan members who take long term maintenance medications to have a choice between obtaining such medications from a mail order pharmacy or a local retail pharmacy outlet, by effectively balancing plan reimbursement and discount payments such that both types of pharmacies are compensated essentially equally, while taking into consideration the relative operational strengths and weaknesses of each type. The consumer thus is pleased, by having a choice of pharmacies based on his/her own perceptions of the merits of each and particularly in not being deprived of such choice because of financial biases in the plan's provisions. The payer also is pleased, since the plan members are content and the plan costs are economically reasonable. The pharmacy industry as a whole also benefits, since undue biases toward mail order are avoided, retail pharmacies can effective participate in the overall dispensing of all medications and each part of the industry is able to compete on the basis of its merits of the customer service and value.

In its basic embodiments, the plan operates by having the PBM set a target cost for medications and dispensing services which it will pay according to contracts it enters into with the pharmacies, and similarly having contracts with its customers (the payers) as to the target costs and its management fees that it will charge the customers under the plan. A key component of this invention is that reimbursement rates are set that benefit the pharmacy, the payer and the consumer. The pharmacy target costs are based on a combination of industry-accepted medication cost schedules and negotiated discounts, calculated such that the payments to the pharmacies will all be substantially equal for a given consumer's medication, dosage and quantity prescription, taking into account the different operating characteristics and costs of retail pharmacies versus mail order pharmacies in terms of factors such as consumer contact and education, economies of scale in inventorying, staffing requirements and the like.

In many of its embodiments the plan of the invention includes a method to ensure that the payer, the pharmacy and the consumer are not disadvantaged. We have called this method the "true-up" feature. A lower of AWP or MAC price model is applied. At the conclusion of a set period of time the reimbursement performance is measured and compared to a guaranteed value. If the value is above or below the targeted discount, the AWP or MAC prices are adjusted ("trued up") to compensate moving forward for the next set time period. These small adjustments are made every set time period to ensure performance balances to an overall guaranteed value. In this manner the payer benefits from the MAC pricing on individual generic products and benefits from assurances that the overall guaranteed performance is maintained, the pharmacy benefits by the assurance that it will be paid at an overall guaranteed discount performance number and the consumer benefits by paying a co-payment that is reflective of the lower of MAC or AWP and thus is not disadvantaged by electing the one time 90-day fill as opposed to having the same prescription filled three separate times for a 30-day supply.

An additional aspect of the current invention is its ability to simplify prescription ordering procedures for the pharmacies. When a pharmacy sends a prescription to a PBM for processing, they utilize a computer system and transmit on-line a request of payment to the PBM. This is called an on-line adjudicated claim. A pharmacy communicates to the PBM by sending an on-line adjudication claim to what is known in the industry as a "switch" company. There are two sets of numbers that are important to this transaction. The first is what is known as the "business identification number" (BIN). The BIN identifies the PBM that is processing the claim. The switch company recognizes this BIN and routes the claim to the appropriate PBM for processing. The second number is known as the PCN, described above. Once a claim has been routed to the appropriate PBM, the PCN directs the claim to the appropriate plan or payer within the PBM for processing. The adjudicated claim contains important information such as patient identification, drug and dosage, and days supply for which the medication is intended to be dispensed. The pharmacy enters this information and then transmits the claim electronically. Once routed to the PBM, the PBM reviews the claim and determines if the patient is eligible, if the drug is approved for dispensing, what portion the patient should pay as a co-payment, and at what rate should the pharmacy be reimbursed. In addition the PBM verifies that the days supply is an approved benefit for the member. As noted in the Background, since the consumer only presents one identification card, availability of different quantities and design benefits for the same medication with different PCNs can cause confusion at the pharmacy. The pharmacy staff member must decide whether to submit to the appropriate BIN the PCN for the 30 day benefit or the PCN for the 90 day benefit. If the incorrect PCN is used, the PBM will reject the claim until the PCN error can be corrected, thus delaying filling of the prescription for the consumer.

The current invention eliminates the need for multiple PCNs for the same medication for a given payer. Under the present plan each medication for a given payer has only a single PCN regardless of the quantity (number of days supply). The pharmacist need only provide the basic data of medication identification, dosage and quantity along with the single PCN for that medication and the BIN for that payer plan. Through editing procedures internal to the PBM itself, the PBM can review the claim and based on the days supply provided by the pharmacist, correctly apply the benefit structure for the member and the appropriate reimbursement to the pharmacy. This unique editing feature enables a pharmacy to have to select and submit only a single PCN for the consumers medication for review. This process saves time and confusion for the consumer and the pharmacy and ensures a greater utilization of the 90 day benefit which saves the payer. This applies not only to retail pharmacies, which may have a only small staff to handle such administrative matters and thus appreciate the simplification of their tasks, but also large mail order pharmacies, since elimination of the need to select among multiple PCNs for many prescriptions may allow staff to be reduced or some staff members to be reassigned to other tasks.

The foregoing, together with other features and advantages of the present invention, will become more apparent when referring to the following specification, claims and accompanying drawings.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

DETAILED DESCRIPTION OF THE INVENTION

When a consumer receives a prescription for medication from a physician, the consumer either goes to a retail pharmacy or utilizes mail order to have the prescription filled. If utilizing a retail pharmacy, the consumer walks into the pharmacy and presents the prescription to a pharmacist or pharmacy staff member. The pharmacy enters the prescription into a computer, which sends the information to a telecommunications switch, or routing, company. Next, the switch company sends the information to the correct PBM with which the pharmacy has contracted for the type of prescription. The PBM determines the benefits the consumer is eligible for, i.e., whether the prescription is eligible for fulfillment based on the terms of the payer plan that the consumer is under. The PBM reports back through the switch company to confirm the amount of medication the consumer is eligible for, copay amount if required, and certain safety messaging if appropriate. In most cases a prescription is approved and filled without question or delay, since the consumer's prescription meets all of the applicable requirements of the plan that the consumer is under. There are, however, a number of common reasons why a prescription may not be approved for fulfillment, which must be reported back to the pharmacy so that the consumer can, if possible, make the necessary corrections or obtain further physician input to allow resubmission of the prescription.

The present invention provides a system and method for a consumer to go to either a retail pharmacy or a mail order pharmacy and have a prescription approved and filled, whether the prescription medication quantity is intended for 30 days or 90 days or any other prescribed time period. Additionally, the retail pharmacy only has to adjudicate the claim to a PBM under a single PCN to obtain a determination of eligibility and of the reimbursement rate. The pharmacist no longer has to determine which of multiple PCNs is correct for a particular plan (BIN) in order to get a prescription request adjudicated by the PBM. Further, since the plan of this invention essentially puts all pharmacies on equivalent financial footing, a consumer can exercise his or her choice in selecting which pharmacy to patronize.

Figure 1:
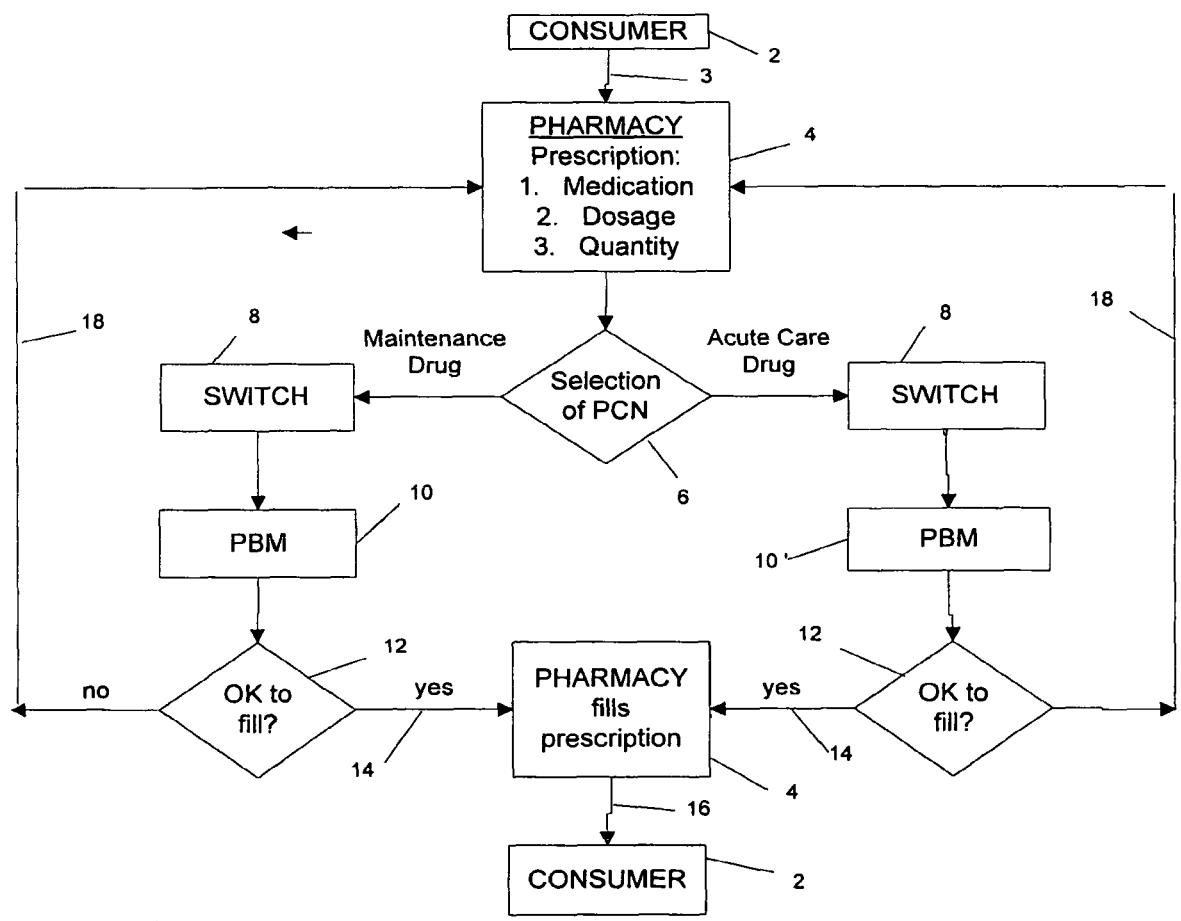
FIG. 1 is a process flow diagram showing the typical routing of a prescription approval and reimbursement request in many of the current prior art plan systems currently in the marketplace.

FIG. 1 outlines the course of a prescription request under many of the prior art commercial plans currently in the marketplace. A consumer 2 at 3 brings a prescription from a physician to a pharmacy 4. The prescription identifies the medication to be dispensed, the dosage of each tablet or other dose unit, and the quantity of dose units to be dispensed. For the purposes of the discussion below, a short term (acute care) dose unit quantity will be considered to be a 30-day quantity and a long-term (maintenance) dose unit quantity will be considered to be a 90-day quantity. The prescription may also indicate whether a brand name medication is required or a generic equivalent may be substituted. The pharmacist or pharmacy staff member selects what he/she believes to be the appropriate PCN for the consumer's plan based on the plan BIN at 6 and sends the request by computer to the switch (routing) company 8, which, based on the BIN and PCN provided by the pharmacist, routes the request to the designated PBM 10 or 10'. The recipient PBM 10 or 10' reviews the request at 12, and if all is in order in the request information and the prescription meets the plan's formulary and eligibility criteria, the PBM at 14 so notifies the pharmacy 4 and the pharmacy 4 fills at 16 fills the consumer 2's prescription.

Such prior art systems may have numerous inherent or deliberate problem areas or biases. One as noted is the requirement that the pharmacy 4 must determine the correct PCN for the consumer's plan. An incorrect PCN designation will result in disapproval of the request and return to the pharmacy for correction at 18. Further, under many of the current plans, especially those in which the PBM owns a "captive" mail order pharmacy and a maintenance medication is involved, the consumer 2 may be required or at least strongly urged financially to select as the pharmacy 4 only the PBMs captive mail order pharmacy, such that the consumer's potential choice of what pharmacy to patronize is curtailed or eliminated right at the entry 3 into the system. (Such financial biasing may be done either by mandating use of a specific pharmacy 4 or by increasing a consumer's required copay or reducing the discount available to the consumer if other than the captive pharmacy is used by the consumer.) Such prior art systems are also often very difficult for PBMs to monitor for optimum performance because important decisions (such as selection of the PCN) are made at different points in the system by different people who may have greater or lesser understandings of the operation of the system.

Figure 2:
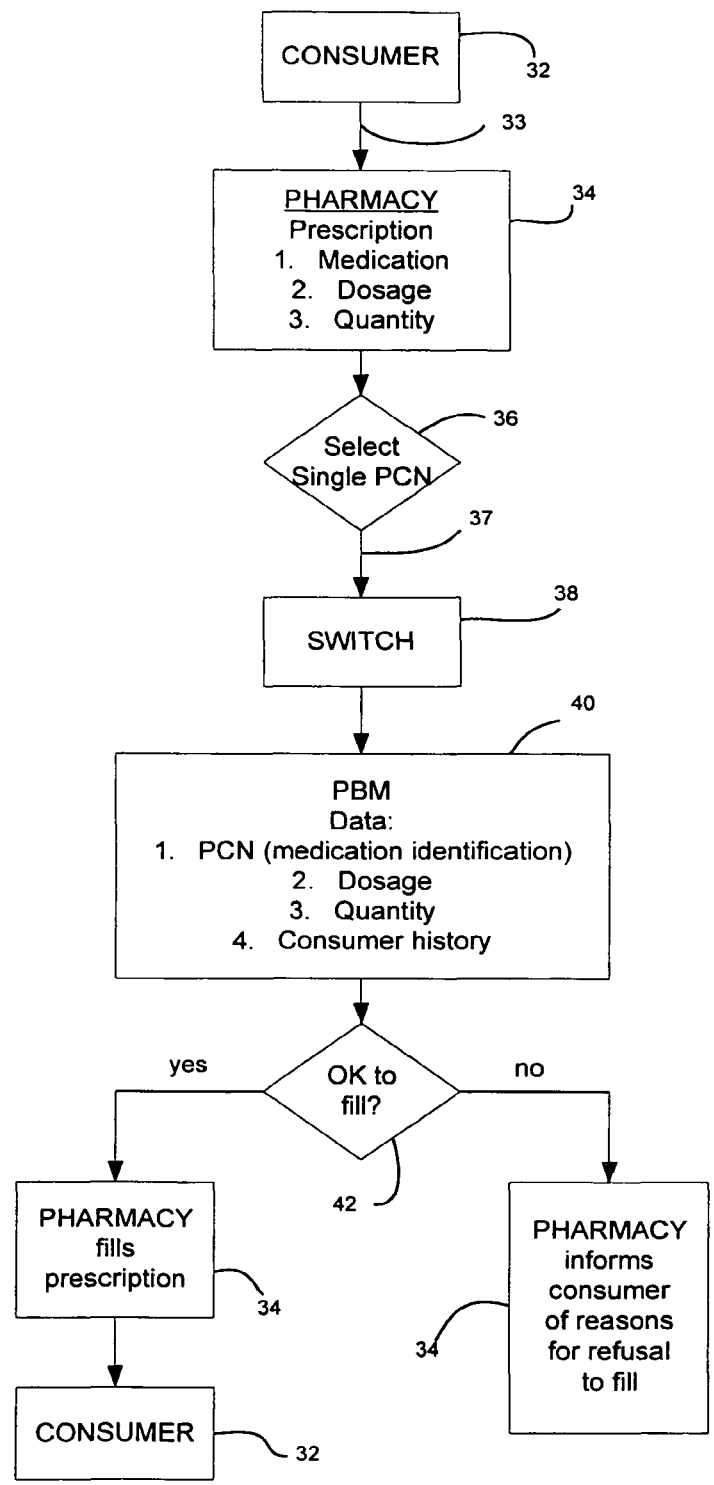
FIG. 2 is a process flow diagram showing the typical routing of a prescription approval and reimbursement request in the method of this invention.

The method of the present invention is outlined in FIG. 2, and will immediately be seen to be much simpler, more direct for both the consumer and pharmacy, and free of biases that would restrict a consumer's choice of pharmacy. It will also be seen that it is much easier to monitor for performance, since at each point the persons involved make decisions only as to those factors which are clearly within their areas of expertise. In the present system, consumer (now designated 32) at 33 takes his/her prescription to any pharmacy 34 of his or her choice. Since under the present plan all pharmacies are will be compensated on a substantially equivalent basis for filling this consumer's particular prescription, there is no element of bias on the part of the pharmacy or the PBM of the consumer's plan for or against any type of pharmacy. At the pharmacy 34 the pharmacist or pharmacy staff member needs only to select a single PCN—the PCN assigned to the medication itself—at 36 and send that PCN, along with the dosage and quantity data, at 37 to the switch company 38 who in turn routes it to the single PBM 40 who handles all requests for that medication. The PBM internally analyzes the request at 42. Knowing the medication itself from the single PCN, the PBM can then assess whether the dosage and quantity prescribed are within the limits of the plan's formulary, and whether filing of the prescription is timely based on the consumer's past prescription fulfillment history. The PBM may also assess whether dispensing of this prescribed medication is appropriate in view of other medications known by the PBM to have been prescribed previously to the consumer. Whether or not the PBM's internal analysis procedures involve assignment of further PCNs, subdivisions thereof, or other procedures in strictly for the PBM to decide, and does not affect the operation of this invention. Importantly, it does not affect the consumer or the pharmacy and does not impose any burdens on them, in contrast to the case with the prior art systems. Once the PBM completes its assessment of the prescription request, it communicates approval or disapproval (with reasons) back to the pharmacy 34 either directly or through the switching company.

The present plan system functions by use by the PBM of contracted discounts and fulfillment service charges between the PBM and the various pharmacies who wish to participate in the plan. The function is best understood by reference to the Table below, in which an exemplary set of discounts, copays and fulfillment fees are presented. It will be understood that the values shown are exemplary only, and that discounts, copays and fees can and do vary widely depending on the contractual terms consented to by the parties to the various agreements. Commonly there may be different terms within a plan for different medication groups or even for different individual medications. Different pharmacies or pharmacy chains may also have different contractual financial terms with the same PBM, notwithstanding that all use the plan concept of the present invention.

In the Table that follows, the present invention is shown in the column at the far right with the current (prior art) retail pharmacy and mail order pharmacy plans being shown in the third and fourth columns from the left. Copays charges to consumers are in the second column, and the Table differentiates between the reimbursement for brand name drugs and generic drugs, which reflects the standard industry practice. "AWP" means "average wholesale price" of a medication or medication group, whether brand name or generic, usually available from a single or limited number of producers, and is commonly a price determined on a national basis independently of the PBM, pharmacy or plan contracts. "MAC" means "maximum allowable cost" of a generic medication, which usually is calculated from consideration of marketplace prices for the medication from different producers. Such pricing data are commercially and publicly available from various sources. The data in the Table are generally presented as a total cost per dispensed dosage quantity, and are in the format of a "list price" such as AWP or MAC followed by the discount from that price that the PBM and the pharmacy have agreed to (e.g., "−15%") and by the fulfillment fee per transaction which the PBM will pay to the pharmacy. It is not uncommon for there to be no fulfillment fee ("+$0") especially in transactions involving generic drugs.

the prior art plans with respect to the mail order pharmacies while, unlike prior art plans, also equally available and attractive to the retail pharmacies.

TABLE 1

Discount and Payment Comparisons

| Medication | Consumer Copay | Retail Pharmacy 90 day quantity | Mail Order Pharmacy 90 day quantity | This Invention |
|---|---|---|---|---|
| Brand Name Drugs | 20%, 30% | AWP − 15% + $2 (3 copays) | AWP − 20% + $0 (1-2.5 copays) | AWP − 20% + $0 (+1-2.5 copays) |
| Generic Drugs | 0%, 10% | Lower of: A) AWP − 15% + $2 B) MAC + $2 (3 copays) | AWP − 50% + $0 (1-2.5 copays) | Target is always AWP − 50% + $0 (with copays) which is obtained by using AWP − 25% + $0 and MAC + $0 in combination |
| Comments: | | Cannot usually compete on long-term prescription pricing and discounts | Usually does not accept short-term prescriptions | Puts retail and mail order pharmacies on equivalent basis for all drugs from consumers' and payers' perspective |

It will be seen from the Table that a major effect of the claimed prescription plan as compared to the prior art is in the handling of reimbursements for generic drugs. Generic drug reimbursement represents a significant share of prescriptions dispenses, generally being about 50% of prescription dispensed nationally. It is also the portion of the industry which is most susceptible to control by the medical reimbursement plans, since there are numerous medication manufacturers for many of the generic drugs, which fosters competition between them, while most of the brand name (proprietary) drugs are available only from a single producer. Generic drugs save money for the payer, provide consumers with the lowest copay option and typically provide the pharmacy with the highest profitability.

The present invention focuses not on the quantity of medication to be dispensed (and thus on the acute care or maintenance purpose of the prescription) but rather on the cost/discount structure of the pharmacy reimbursement. Effectively the retail pharmacies are given the opportunity to compete for fulfillment of both long-term and short-term prescriptions, but equalizing the reimbursements available under the plan. The plan, unlike the prior art plans, does not bias consumers toward the mail order pharmacies, which many PBMs have assumed must have larger economies of scale, staffing and other financial factors as compared to the retail pharmacies. Such assumptions may not always be correct, according to some studies, but the relative merits of the two types of pharmacies is not a factor in the present invention, which instead is focused on giving the consumer the ability to make his or her own evaluation and selection of which type of pharmacy to patronize. It will be seen from the Table that a PBM using the present plan will target a reimbursement rate generally comparable to the rate accorded to mail ordered pharmacies in the past, but does so in a manner which reflects and utilizes rate structures equally available to both types of pharmacies. This use of different criteria to achieve a similar rate level represents a completely novel and advantageous element of the present invention. Thus rather than rigidly applying a single measurement based solely on AWP, as the prior art plans did, the present plan uses a blend of AWP and MAC criteria, and adjusts these as appropriate so that the overall reimbursement offered to pharmacies makes this plan competitive with Consumers can be adversely affected if a true-up process is not established, since without such a provision a consumers copayments for a 90-day supply could exceed three times the traditional 30-day retail copayment.

Similar adjustments by the PBM can be negotiated and agreed to in contracts with retail pharmacies with respect to the dispensing fees to be paid under the plan. Prior art plans have worked on the basis that dispensing costs are higher for retail pharmacies because of staffing costs and lower volume over which to expense the per-consumer dispensing costs. Increasing a retail pharmacy's proportion of dispensing of large quantity maintenance drug prescriptions offers an opportunity for the PBM and the retail pharmacy to reduce or eliminate the dispensing fee portion of reimbursement, thus reducing the costs to be passed along to the payer by the PBM.

An important optional (but preferred) element in the present invention is a function of continually reviewing the performance of the pharmacies in cost control, and particularly in the area of cost reduction by increasing the proportion of lower cost generic drugs in the overall mix of dispensed drugs. In the past mail order pharmacies and some mandate plans have accomplished this simply by requiring substitution of generics unless a physician has required otherwise. The present invention also optionally allows for a particularly productive approach which involves education of the consumers so that they recognize when generic medications are equally acceptable in their own personal health and treatment as are brand name drugs. Education is in the realm of both the PBM and the pharmacist, and the present invention uses the involvement of both. Contracts with pharmacies can include provisions that encourage pharmacists to communicate with their consumers about the value of generic drugs, which is especially effective in the retail pharmacy setting where the pharmacist and the consumer meet directly. The PBM also can communicate the same message through its regular communications with payers and their employees and members. The pharmacy makes its highest profit margin dispensing the generic drug. The PBM that owns the mail order pharmacy may drive higher cost brands to maximize the formulary rebate income.

In keeping with this purpose, the present plan optionally but preferably includes not only the PBM's continual review of performance of all pharmacies participating in the plan, but also periodic adjustment of the discount and cost structures to reward those pharmacies who are operating at greater-than-expected performance and, conversely, to provide incentive to under-performing pharmacies to improve. This method, which we have designated "truing up" or the "true-up" feature, ensures that the payer, the pharmacy and the consumer are not disadvantaged. A lower of AWP or MAC price model is applied. At the conclusion of a set period of time the reimbursement performance is measured and compared to a guaranteed value. If the value is above or below the targeted discount for the period, the AWP or MAC price discounts are adjusted to compensate moving forward for the next set time period. If the drug mix has overperformed, the reimbursement is increased, as for instance by reducing the discount taken by the PBM (e.g., from a 50% discount to a 49% discount), so that discounted amount paid to the pharmacy is increased and it therefore receives a greater income. On the other hand, if the drug mix has underperformed, the discount can be increased (e.g., from a 50% discount to a 51% discount) so that reimbursement—i.e., the discounted amount paid—is reduced, which it is expected will encourage the pharmacy to improve its performance over the next period so that its discount can be lowered and its reimbursement increased. Compiling performance data and making the appropriate analyses to allow such adjustments to be made require significant internal data collection and processing capabilities by the PBMs. However, such capabilities are already possessed by some PBMs and others can be expected to acquire similar capabilities in the near future, since having these small adjustments made every set time period (e.g., quarterly) ensure performance balances to an overall guaranteed value.

By use of the truing up feature, the payer benefits from the MAC pricing on individual generic products and benefits from assurances that the overall guaranteed performance is maintained, the pharmacy benefits by the assurance that it will be paid at an overall guaranteed discount performance number, and the consumer benefits by paying a co-payment that is reflective of the lower of MAC or AWP and thus is not disadvantaged by electing the one time 90 day fill as opposed to having the same prescription filled three times for 30-day supplies.

Separately, the plan of this invention also involves contractual agreements between the PBM and the payers who wish to provide the PBM's plan to their employees, members, or other affiliated people. Such payers are commonly business entities such as health plans, companies, partnerships or corporations, whether large, mid-sized or small, governments or governmental agencies, trade unions and non-governmental organizations or associations. Each payer contracts with the PBM for the specific pharmacy services and medication costs and fees that it is willing to reimburse, based on the PBM's having obtained discounted costs from the pharmacies, as well as the contracted fee that the payer is willing to pay the PBM for managing the plan for it and its employees or members. As with the pharmacy contracts, the payer contracts will also vary depending on what formulary a payer is willing to reimburse for, how many members or employees the payer has, and so forth.

It is to be expected that PBMs which have cost driven plans which focus primarily on mandating or influencing consumers to use mail order pharmacies to fill maintenance prescriptions, especially those who own mail order pharmacies; will initially see little value in adopting the present invention. However, it is anticipated that the present plan's focus on providing the ability to consumers to be able to patronize the pharmacy of their choice for all of the prescription medication needs, whether acute care or maintenance medications, will be sufficiently attractive to such consumers that they will encourage their employers or organizations as payers to obtain and adopt such plans. The employers and organizations, in turn, will demand of PBMs that they make such plans available to the payer community, in preference to mandated or biased plans. Under such conditions, it is to be expected that the plans of the present invention will rapidly gain market share and enhance the ability of people to be able to influence or control their own costs of health care and prescription drugs.

Although several embodiments of the invention have has been described above by way of example only, it will be understood by those skilled in the field that numerous variations and modifications may be made to the disclosed embodiments without departing from the scope or spirit of the invention, as it is defined by the appended claims.

We claim:

1. A computer-implemented system comprising:
a computer network;
a client device communicatively coupled to the computer network, the client device configured to receive order information representative of a prescription drug, the order information including a given plan payer and a quantity of the prescription drug;
a telecommunications switch communicatively coupled to the client device via the computer network, the telecommunications switch configured to receive one or more processor control numbers (PCNs) associated with the order information and route the order information based on the one or more (PCNs), a PCN being independent of the quantity of the prescription drug and the PCN uniquely identifying the prescription drug; and
a controller communicatively coupled to the client device and the telecommunications switch via the computer network, the controller configured for:
receiving prescription information about the prescription drug, the prescription information comprising the given plan payer, a dosage, the quantity and a day value indicative of number of days supply for the prescription drug, the prescription information being processed in the computer network in which the telecommunications switch is configured to communicate with a plurality of prescription benefit manager (PBM) systems, wherein the telecommunications switch is configured to mute the one or more PCNs to at least one of a first PBM system and a second PBM system, the first PBM system and the second PBM system being configured to approve the prescription drug;
determining a single PCN for the given plan payer, in response to receiving the prescription information;
forwarding the single PCN to the telecommunications switch, the telecommunications switch configured to communicate with the first PBM system for allowing for the first PBM system to approve the prescription drug based on the single PCN, regardless of the quantity of the prescription drug;
determining a reimbursement for the order, the reimbursement being equal to the lesser of a first value calculated based on a maximum allowable cost (MAC) and a second value calculated based on an average wholesale price (AWP), wherein at least one of the MAC and the AWP is adjusted in response to a difference between a guaranteed value and a reimbursement performance for a plurality of orders over a time period; and transmitting an authorization to a pharmacy computer system to allow filling of the prescription independent of the quantity of prescription drug indicated, eliminating the need for the pharmacy computer system to assign multiple PCNs for different number of days supply and the need to select from among a plurality of communications switches to communicate with the plurality of PBM systems.

2. A computer-implemented system comprising:

a computer network;

a client device communicatively coupled to the computer network, the client device configured to receive order information representative of a prescription drug, the order information including a given plan payer and a quantity of the prescription drug;

a telecommunications switch communicatively coupled to the client device via the computer network, the telecommunications switch configured to receive one or more processor control numbers (PCNs) associated with the order information and route the order information based on the one or more PCNs, a PCN being independent of the quantity of the prescription drug and the PCN uniquely identifying the prescription drug; and one or more processors communicatively coupled to the client device and the telecommunications switch via the computer network, the one or more processors configured for executing one or more logic instructions, wherein the logic instructions when executed by the one or more processors cause the system to:

receive prescription information about the prescription drug, the prescription information comprising the given plan payer, a dosage, the quantity and a day value indicative of number of days supply for the prescription drug, the prescription information being communicated in the computer network in which the telecommunications switch is configured to communicate with a plurality of prescription benefit manager (PBM) systems, wherein the telecommunications switch is configured to route the one or more PCNs to at least one of a first PBM system and a second PBM system, the first PBM system and the second PBM system being configured to approve the prescription drug;

determine a single PCN for the given plan payer, in response to receiving the prescription information, forward the single PCN to the telecommunications switch, the telecommunications switch configured to communicate with the first PBM system for allowing for the first PBM system to approve the prescription drug based on the single PCN, regardless of the quantity of the prescription drug;

determine a reimbursement for the order, the reimbursement being equal to the lesser of a first value calculated based on a maximum allowable cost (MAC) and a second value calculated based on an average wholesale price (AWP), wherein at least one of the MAC and the AWP is adjusted in response to a difference between a guaranteed value and a reimbursement performance for a plurality of orders over a time period; and transmit an authorization to a pharmacy computer system to allow filling of the prescription independent of the quantity of prescription drug indicated, eliminating the need for the pharmacy computer system to assign multiple PCNs for different number of days supply and the need to select from among a plurality of communications switches to communicate with the plurality of PBM systems.

3. A non-transitory computer-readable storage medium comprising at least one program for execution by one or more processors of a first device, the at least one program including instructions which, when executed by the one or more processors, cause the first device to perform operations comprising:

receiving, using the one or more processors and via a computer network, prescription information about a prescription drug, the prescription information comprising a given plan payer, a dosage, a quantity and a day value indicative of number of days supply for the prescription drug, the prescription information being processed in the computer network in which a telecommunications switch is configured to communicate with a plurality of prescription benefit manager (PBM) systems, the telecommunications switch being communicatively coupled to a client device via the computer network, the client device configured to receive order information representative of the prescription drug via the computer network, the order information including the given plan payer and the quantity of the prescription drug, wherein the telecommunications switch is configured to route one or more processor control numbers (PCNs) to at least one of a first PBM system and a second PBM system, the first PBM system and the second PBM system being configured to approve the prescription drug;

determining, using the one or more processors, a single PCN for the given plan payer, in response to receiving the prescription information, the PCN uniquely identifying the prescription drug independent of the quantity of the requested prescription drug, the telecommunications switch configured to receive one or more PCNs associated with the order information and route the order information based on the one or more PCNs;

forwarding, using the one or more processors, the single PCN to the telecommunications switch, the telecommunications switch configured to communicate with the first PBM system to allow for the first PBM system to approve the prescription drug based on the single PCN, regardless of the quantity of the requested prescription drug;

determining, using the one or more processors, a reimbursement for the order, the reimbursement being equal to the lesser of a first value calculated based on a maximum allowable cost (MAC) and a second value calculated based on an average wholesale price (AWP), wherein at least one of the MAC and the AWP is adjusted in response to a difference between a guaranteed value and a reimbursement performance for a plurality of orders over a time period; and transmitting, using the one or more processors, an authorization to a pharmacy computer system to allow filling of the prescription independent of the quantity of prescription drug indicated, eliminating the need for the pharmacy computer system to assign multiple PCNs for different number of days supply and the need to select from among a plurality of communication switches to communicate with the plurality of PBM systems, wherein the one or more processors are communicatively coupled to the client device and the telecommunications switch via the computer network.

* * * * *